US012102739B2

(12) United States Patent
Camarero Díez et al.

(10) Patent No.: US 12,102,739 B2
(45) Date of Patent: Oct. 1, 2024

(54) SUPPORT FOR VOLATILE SUBSTANCE-DIFFUSING WICKS

(71) Applicant: ZOBELE HOLDING S.P.A., Trento (IT)

(72) Inventors: Roberto Camarero Díez, Barcelona (ES); Jordi Masó Sabaté, Barcelona (ES)

(73) Assignee: ZOBELE HOLDING S.P.A., Trento (IT)

( * ) Notice: Subject to any disclaimer, the term of this patent is extended or adjusted under 35 U.S.C. 154(b) by 28 days.

(21) Appl. No.: 16/958,205

(22) PCT Filed: Dec. 26, 2018

(86) PCT No.: PCT/EP2018/086884
§ 371 (c)(1),
(2) Date: Jun. 26, 2020

(87) PCT Pub. No.: WO2019/129789
PCT Pub. Date: Jul. 4, 2019

(65) Prior Publication Data
US 2021/0069370 A1    Mar. 11, 2021

(30) Foreign Application Priority Data

Dec. 27, 2017  (ES) .............................. ES201731475

(51) Int. Cl.
*A61L 9/12*         (2006.01)
*A01M 1/20*         (2006.01)
(52) U.S. Cl.
CPC ............ *A61L 9/127* (2013.01); *A01M 1/2044* (2013.01); *A61L 2209/15* (2013.01)

(58) Field of Classification Search
CPC .... A61L 9/127; A61L 2209/15; A01M 1/2044
USPC .......................................................... 239/44
See application file for complete search history.

(56) References Cited

U.S. PATENT DOCUMENTS

| | | | | |
|---|---|---|---|---|
| 3,028,100 A | * | 11/1958 | Xenakis et al. ....... | A45D 34/04 239/47 |
| 4,293,095 A | * | 10/1981 | Hamilton ................ | A61L 9/127 239/35 |
| 4,323,193 A | * | 4/1982 | Compton ................ | A61L 9/127 239/44 |
| 4,372,490 A | * | 2/1983 | Le Caire, Jr. ............. | A61L 9/12 220/4.24 |

(Continued)

FOREIGN PATENT DOCUMENTS

| EP | 1 103 479 A1 | 5/2001 |
|---|---|---|
| WO | 2006/004891 A1 | 1/2006 |

(Continued)

OTHER PUBLICATIONS

International Search Report received for PCT Patent Application No. PCT/EP2018/086884 mailed on May 20, 2019, 4 page.

(Continued)

*Primary Examiner* — Chee-Chong Lee
(74) *Attorney, Agent, or Firm* — Amster, Rothstein & Ebenstein LLP

(57) ABSTRACT

A support for volatile substance-diffusing wicks including a housing for placing a volatile substance-diffusing wick. The housing is formed by a plurality of elastic extensions defining a funnel shape.

4 Claims, 2 Drawing Sheets

(56) References Cited

U.S. PATENT DOCUMENTS

| | | | | |
|---|---|---|---|---|
| 4,477,414 | A | * | 10/1984 | Muramoto ............... B01D 1/00 261/95 |
| 4,549,693 | A | * | 10/1985 | Barlics ..................... A61L 9/12 206/0.5 |
| 4,739,928 | A | * | 4/1988 | O'Neil .................... A61L 9/127 239/45 |
| 6,354,513 | B1 | * | 3/2002 | Basaganas Millan .... A61L 9/12 239/47 |

FOREIGN PATENT DOCUMENTS

| WO | 2006/061803 A1 | 6/2006 |
|---|---|---|
| WO | 2008/036263 A2 | 3/2008 |
| WO | 2008/036263 A3 | 8/2008 |

OTHER PUBLICATIONS

Written Opinion received for PCT Patent Application No. PCT/EP2018/086884, 5 page.

* cited by examiner

SUPPORT FOR VOLATILE SUBSTANCE-DIFFUSING WICKS

This application is a National Stage entry under 35 U.S.C. 371 of International Patent Application No. PCT/EP2018/086884, filed on Dec. 26, 2018, which claims priority from Spanish Patent Application No. P201731475, filed Dec. 27, 2017, the entire contents of each of which are incorporated by reference herein.

FIELD

The present invention relates to a support for volatile substance-diffusing wicks, particularly a support which is placed in the neck of a liquid-filled container.

BACKGROUND OF THE INVENTION

Volatile substance diffusers formed by a container, for example, a bottle, filled with a liquid containing volatile substances, are commonly used. For the diffusion of these volatile substances, a wick which is impregnated with liquid at one of its ends and exposed to the open air at the other end, diffusing volatile substances, is used.

In order to place the wick in a substantially vertical position so that it can diffuse the volatile substances properly, a certain type of support comprising a housing for placing the wick is often used.

The drawback of these supports used today is that they do not prevent the wick from being voluntarily removed for reuse or the liquid from coming out accidentally, for example, in the event of the container tipping over. This is particularly important if the liquid spills over as it usually contains aggressive substances, such as solvents, which can damage the surface on which the container is placed.

Therefore, an objective of the present invention is to provide a support for volatile substance-diffusing wicks which prevents, or at least limits, the accidental spillage of the liquid inside the container where the support is mounted.

Another objective of the present invention is to provide a support for volatile substance-diffusing wicks which prevents the wick from being removed for reuse.

SUMMARY OF THE INVENTION

The mentioned drawbacks are solved with the support for wicks of the invention, having other advantages that will be described below.

The support for volatile substance-diffusing wicks according to the present invention comprises a housing for placing a volatile substance-diffusing wick, and is characterized in that said housing is formed by a plurality of elastic extensions defining a funnel shape.

The wick can thereby be placed in said housing and the elastic extensions will hold said wick to prevent the removal thereof, preventing reuse. Furthermore, said funnel-shaped elastic extensions prevent the liquid from coming out accidentally, or limit same, when the support according to the present invention is mounted in a liquid-filled container.

Advantageously, the support for volatile substance-diffusing wicks according to the present invention also comprises at least one holding element for holding the support on a container, for example, a plurality of legs, each with a protrusion at its distal end.

Said plurality of elastic extensions are preferably spaced from one another by means of slots, and according to a preferred embodiment each elastic extension has a trapezoidal shape.

The support for volatile substance-diffusing wicks also preferably comprises a circumferential flange, particularly placed in the upper part thereof, according to its usage position.

Advantageously, the support for volatile substance-diffusing wicks is made of an elastic plastic material, such as polyethylene terephthalate (PET), polyethylene (PE), polypropylene (PP), acrylonitrile butadiene styrene (ABS), nylon, or any other molded material.

BRIEF DESCRIPTION OF THE DRAWINGS

To better understand what has been set forth, drawings in which a practical embodiment is schematically shown only by way of non-limiting example are attached.

DESCRIPTION OF A PREFERRED EMBODIMENT

Figure 1:
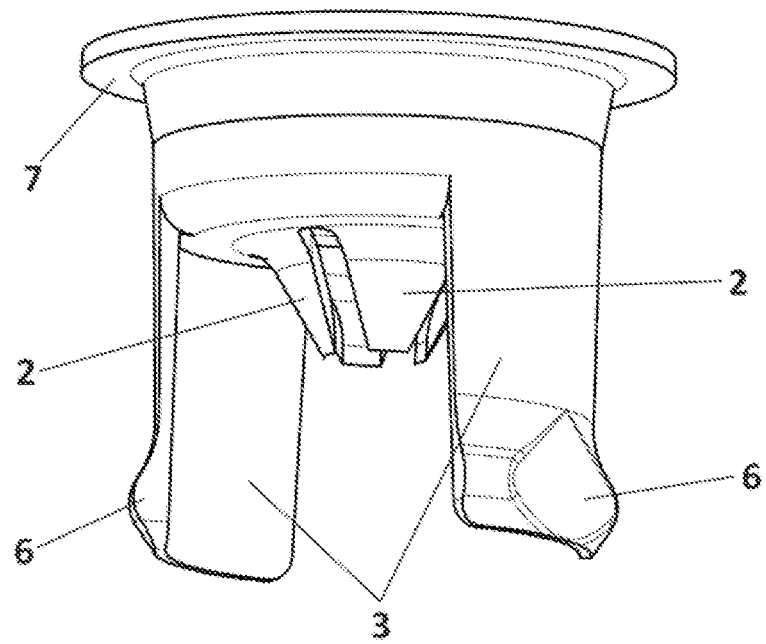
FIG. 1 is a side perspective view of the support for volatile substance-diffusing wicks according to the present invention.

As shown in the drawings, the support for volatile substance-diffusing wicks according to the present invention is placed in a container 4, for example, a bottle, containing liquid which allows the diffusion of volatile substances, particularly perfume. Specifically, the support according to the present invention is coupled in the mouth of said container 4, as can be seen in FIG. 3.

Figure 3:
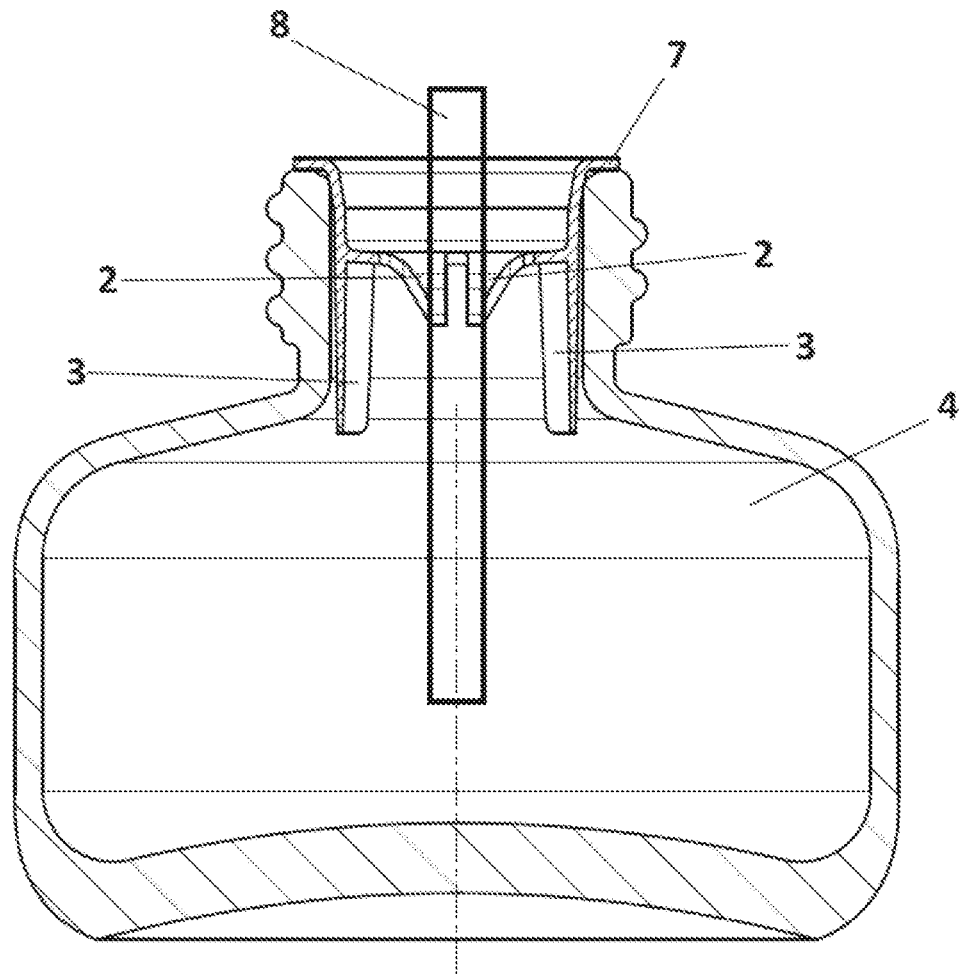
FIG. 3 is an elevational sectioned view of the support for volatile substance-diffusing wicks according to the present invention, placed in a container.

The wick support according to the present invention comprises a housing 1 for placing a wick 8, depicted in FIG. 3. In this position, the wick 8 is placed substantially vertical in its usage position, being in contact with the liquid of the container 4 and is exposed to the open air to allow diffusion of the volatile substances.

The wick 8 is flexible and can be any soft material with capillary properties, such as textiles, cords made with different materials, non-woven fabrics, natural and/or artificial fibers, among others.

If desired, the wick 8 can be connected to a fragrance-diffusing element (not depicted in the drawings), for example, an element having a flower shape or other shapes, woods with capillary properties, or it can be a suitable cord wick acting as the fragrance diffuser itself.

Figure 2:
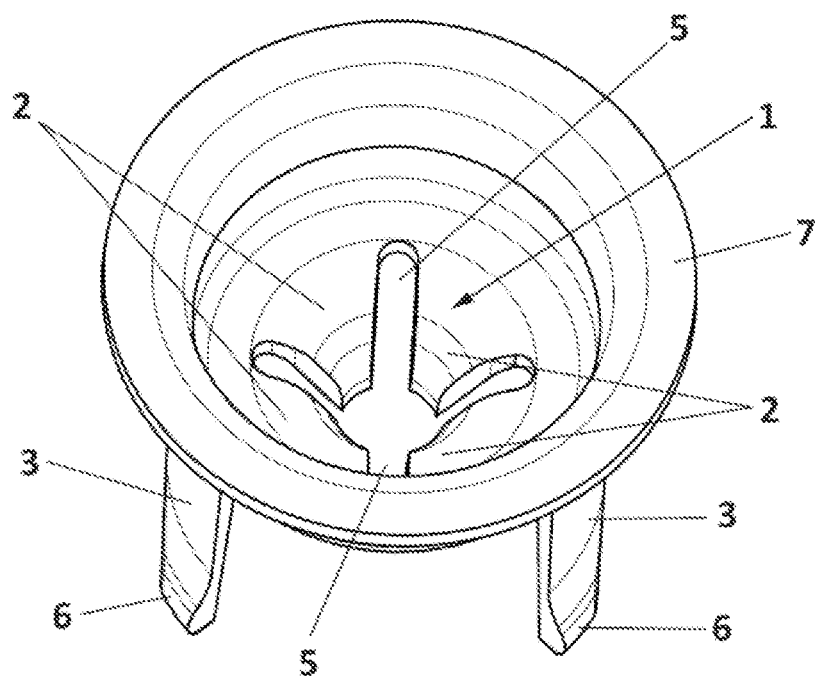
FIG. 2 is a top perspective view of the support for volatile substance-diffusing wicks according to the present invention.

Said housing 1 is formed by a plurality of elastic extensions 2, defining a central hole between them, as seen in FIG. 2. Said elastic extensions 2 as a whole define a funnel shape which prevents the wick 8 from being removed for reuse and the liquid inside the container 4 from coming out, for example, if said container 4 tips over, or at least limits same.

Said elastic extensions 2 are preferably spaced from one another by means of slots 5, and each elastic extension 2 has a substantially trapezoidal shape, as can be seen in FIGS. 1 and 2.

Therefore, by introducing the wick 8 in the housing 1, the elastic extensions 2 will elastically deform adapting to the width or diameter of the wick 8, creating a close contact between the wick 8 and the elastic extensions 2, with the wick 8 being held and a substantially liquid-tight closure being formed.

To hold the support in place in the container 4, the support comprises holding means formed, according to the depicted embodiment, by means of holding legs 3 comprising a protrusion 6 at their distal end, i.e., at the end that is introduced the farthest into the container 4, as seen in FIG. 3.

These holding legs 3 must be elastic enough to allow the introduction thereof into the container 4 and also to hold the support to prevent its removal, preventing tampering of the support.

Furthermore, the support according to the present invention also comprises a circumferential flange 7 in its upper part, in the usage position depicted in FIG. 3. This circumferential flange 7 abuts with the upper edge of the container 4, preventing the support from being completely introduced into the container 4.

The support is made entirely by means of molding, preferably of a plastic material with elastic features, such as polyethylene terephthalate (PET), polyethylene (PE), polypropylene (PP), acrylonitrile butadiene styrene (ABS), nylon, or any other molded material, although it may be any suitable material.

Furthermore, the elastic extensions 2 forming the housing 1 can be made from a suitable elastic material different from the rest of the support.

Although reference has been made to a specific embodiment of the invention, it is obvious for one skilled in the art that the support for wicks described is susceptible to a number of variations and modifications, and that all the mentioned details can be replaced with other technically equivalent details without departing from the scope of protection defined by the attached claims.

The invention claimed is:

1. A support for volatile substance-diffusing wicks, comprising a housing for placing a volatile substance-diffusing wick, wherein said housing comprises:
    an upper portion comprising a bottom wall and a substantially vertical sidewall that intersects with the bottom wall, the bottom wall having an opening through which extends a central axis of the support, the substantially vertical sidewall comprising an outwardly extending circumferential flange configured for abutment with an upper edge of a container to prevent the support from complete introduction into the container; and
    a lower portion comprising:
        a plurality of elastic extensions, each of the plurality of elastic extensions comprising curved inner and outer walls that extend downwards and inwards with an increasing slope along a common curved plane from the bottom wall opening towards the central axis so as define a funnel having a conical shape and so as to form a circular opening in communication with the bottom wall opening, each of the plurality of elastic extensions having a width in a circumferential direction of the circular opening that decreases from the bottom wall opening to bottom ends of the elastic extension; and
        a plurality of slots formed between the plurality of elastic extensions, each of the plurality of slots extending from the bottom wall opening to the bottom ends of the elastic extensions so that the plurality of slots form gaps between the plurality of elastic extensions around the circular opening;
    wherein the support for volatile substance-diffusing wicks further comprising at least one holding element for holding the support on a container; wherein said at least one holding element comprises a plurality of legs, each with a protrusion at a distal end.

2. The support for volatile substance-diffusing wicks according to claim 1, wherein each elastic extension has a trapezoidal shape.

3. The support for volatile substance-diffusing wicks according to claim 1, wherein said housing is made of an elastic plastic material.

4. The support for volatile substance-diffusing wicks according to claim 1, wherein the funnel comprises a top portion that defines a flat annular plane and the plurality of legs extend downward from an outer peripheral portion of the flat annular plane.

* * * * *